(12) United States Patent
Fleming

(10) Patent No.: US 11,246,738 B2
(45) Date of Patent: Feb. 15, 2022

(54) USER WEARABLE URINAL BAG CONCEALMENT DEVICE

(71) Applicant: George Fleming, Richmond, VA (US)

(72) Inventor: George Fleming, Richmond, VA (US)

(*) Notice: Subject to any disclaimer, the term of this patent is extended or adjusted under 35 U.S.C. 154(b) by 343 days.

(21) Appl. No.: 16/296,522

(22) Filed: Mar. 8, 2019

(65) Prior Publication Data

US 2020/0281760 A1    Sep. 10, 2020

(51) Int. Cl.
*A61F 5/44* (2006.01)
*A61F 5/453* (2006.01)

(52) U.S. Cl.
CPC ............ *A61F 5/4408* (2013.01); *A61F 5/453* (2013.01)

(58) Field of Classification Search
CPC ......... A61F 5/4408; A61F 5/453; A61F 5/449
USPC ....................................................... 604/353
See application file for complete search history.

(56) References Cited

U.S. PATENT DOCUMENTS

| 508,229 | A | | 11/1893 | Marcy | |
|---|---|---|---|---|---|
| 2,756,751 | A | | 7/1956 | Smith | |
| 5,607,412 | A | * | 3/1997 | Brown | A61F 5/445 2/46 |
| 9,295,289 | B2 | | 3/2016 | James | |
| D757,399 | S | | 5/2016 | Kalfax | |
| 10,307,305 | B1 | * | 6/2019 | Hodges | A61F 5/4408 |
| 2005/0091722 | A1 | * | 5/2005 | Walsh | A41D 13/04 2/48 |
| 2008/0148769 | A1 | * | 6/2008 | Higgins | A61F 7/02 62/530 |
| 2008/0208149 | A1 | | 8/2008 | Vasquez | |
| 2010/0300453 | A1 | * | 12/2010 | Wells | A61F 5/41 128/844 |
| 2016/0256312 | A1 | * | 9/2016 | Mastracci | A47K 11/12 |
| 2019/0254353 | A1 | * | 8/2019 | Patton | A41B 9/026 |

FOREIGN PATENT DOCUMENTS

KR           200485040 Y1 * 11/2017

* cited by examiner

*Primary Examiner* — Kai H Weng
*Assistant Examiner* — Seth Han

(57) ABSTRACT

A user wearable urinal bag concealment device for discrete public urination includes a first panel and a second panel. The second panel has a lower edge and opposing side edges that are coupled to a front face of the first panel to define a pouch that accessible at an upper edge of the second panel. A plurality of couplers that is coupled to an upper limit of the first panel is configured to couple the first panel to a male user so that the first panel is positioned over and substantially conceals a groin area of the male user. A slot is positioned in the first panel. The pouch is configured to position a urinal bag and to insert hands of the user, positioning the user to manipulate his penis through the slot into an open end of the urinal bag to discretely collect his urine.

17 Claims, 5 Drawing Sheets

USER WEARABLE URINAL BAG CONCEALMENT DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to concealment devices and more particularly pertains to a new concealment device for discrete public urination.

BRIEF SUMMARY OF THE INVENTION

An embodiment of the disclosure meets the needs presented above by generally comprising a first panel and a second panel. The second panel has a lower edge and opposing side edges that are coupled to a front face of the first panel to define a pouch that accessible at an upper edge of the second panel. A plurality of couplers that is coupled to an upper limit of the first panel is configured to couple the first panel to a male user so that the first panel is positioned over and substantially conceals a groin area of the male user. A slot is positioned in the first panel. The pouch is configured to position a urinal bag and to insert hands of the user, positioning the user to manipulate his penis through the slot into an open end of the urinal bag to discretely collect his urine.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
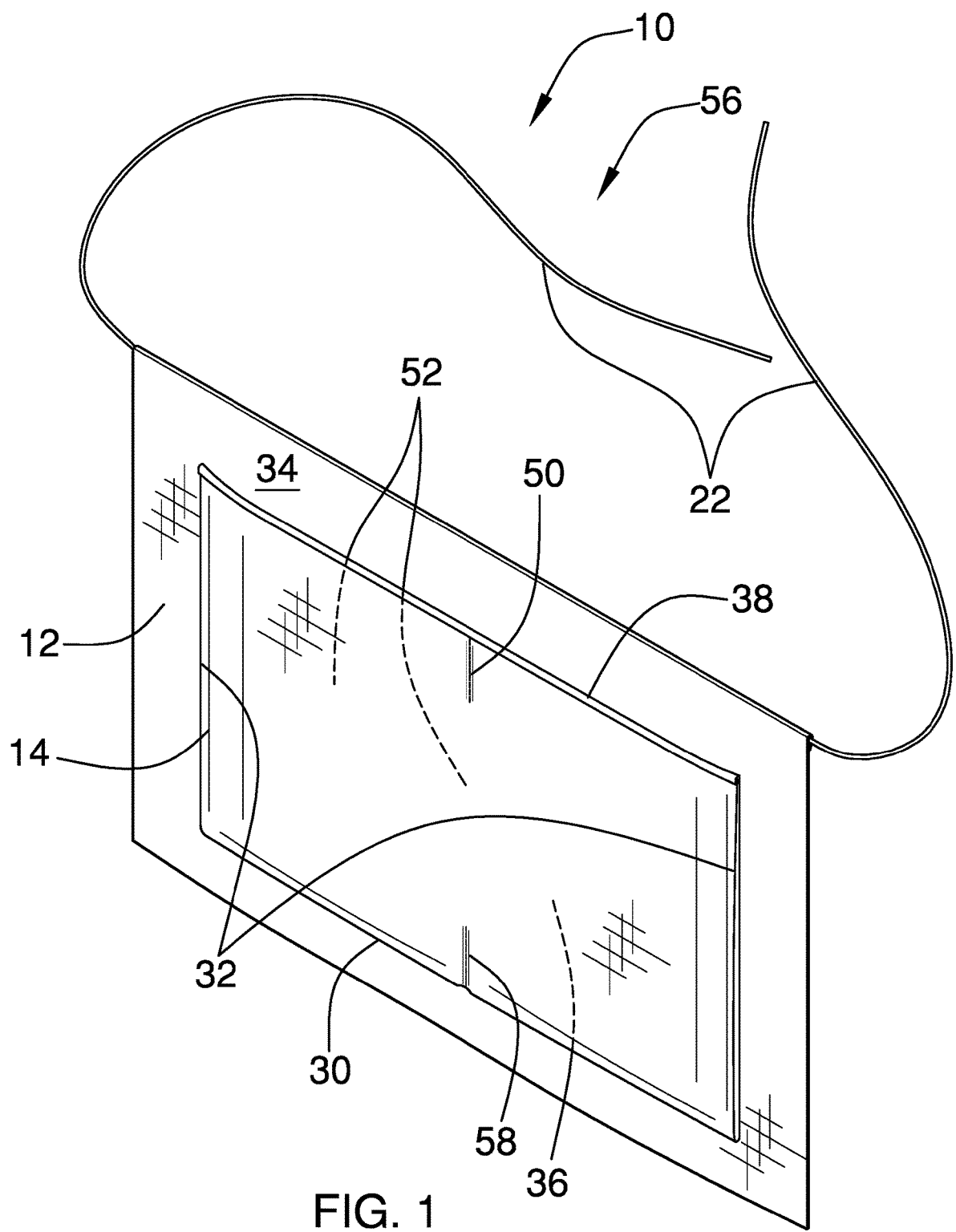
FIG. 1 is a front isometric perspective view of a user wearable urinal bag concealment device according to an embodiment of the disclosure.
Figure 2:
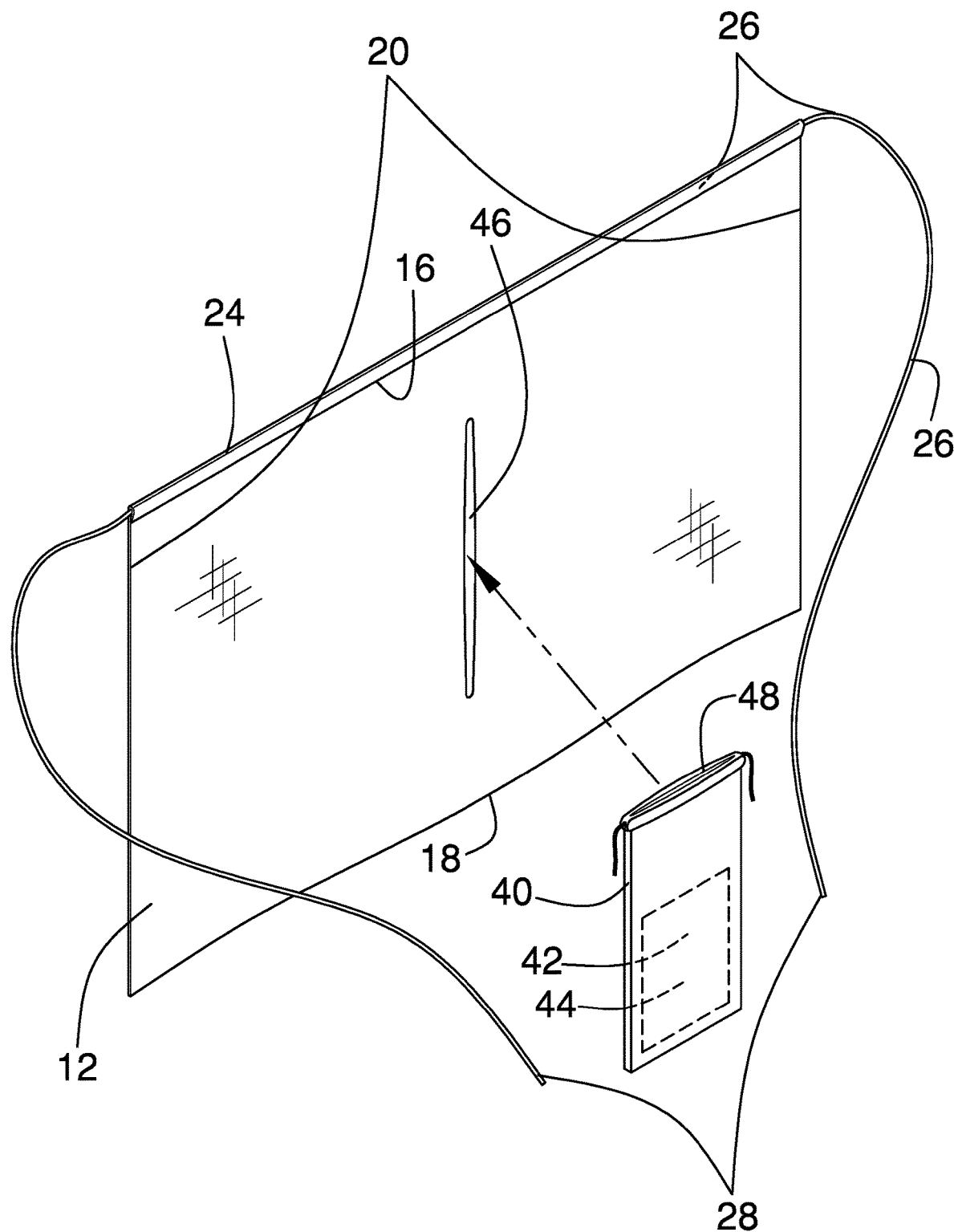
FIG. 2 is a rear isometric perspective view of an embodiment of the disclosure.
Figure 3:
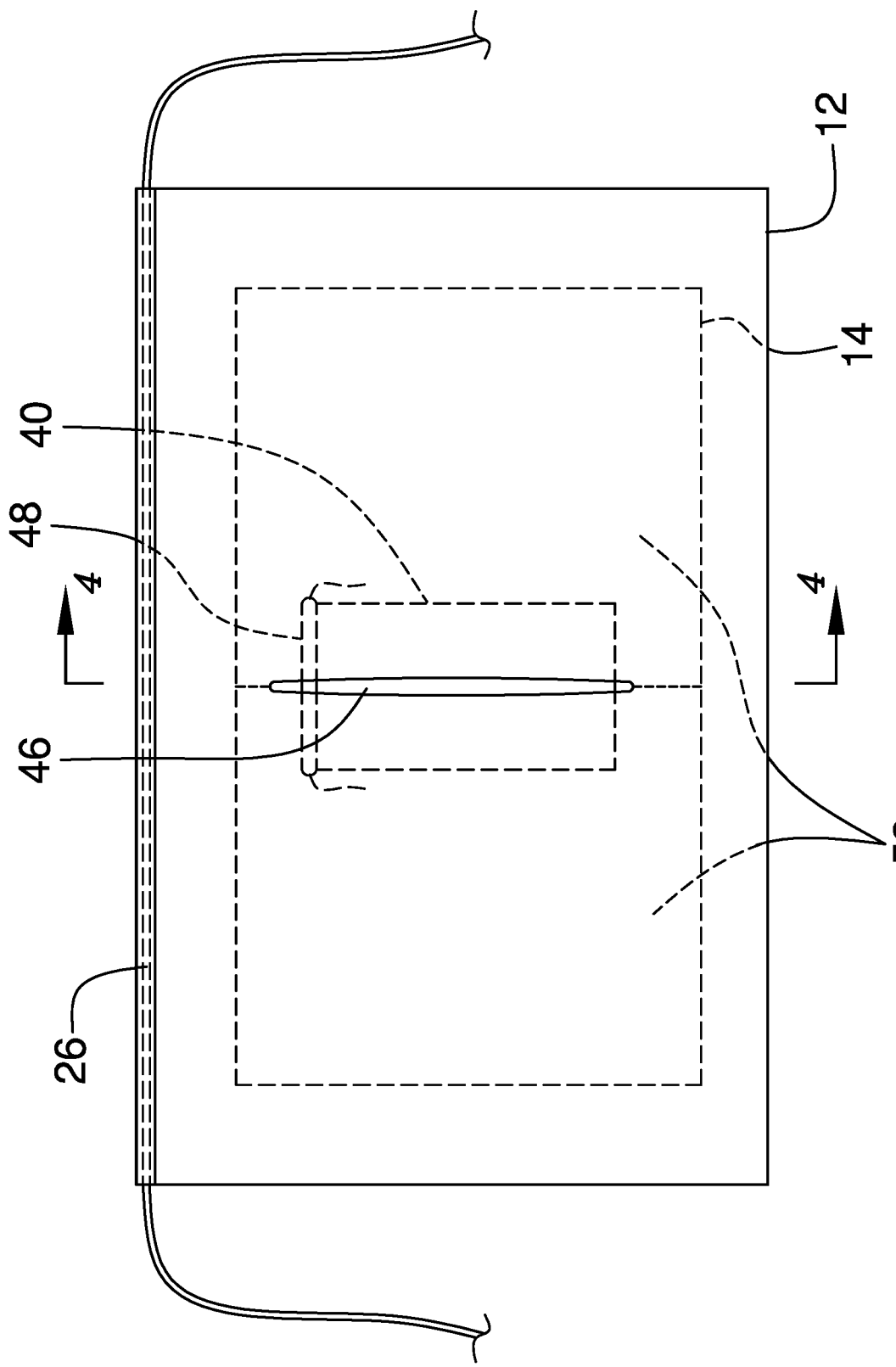
FIG. 3 is a rear view of an embodiment of the disclosure.
Figure 4:
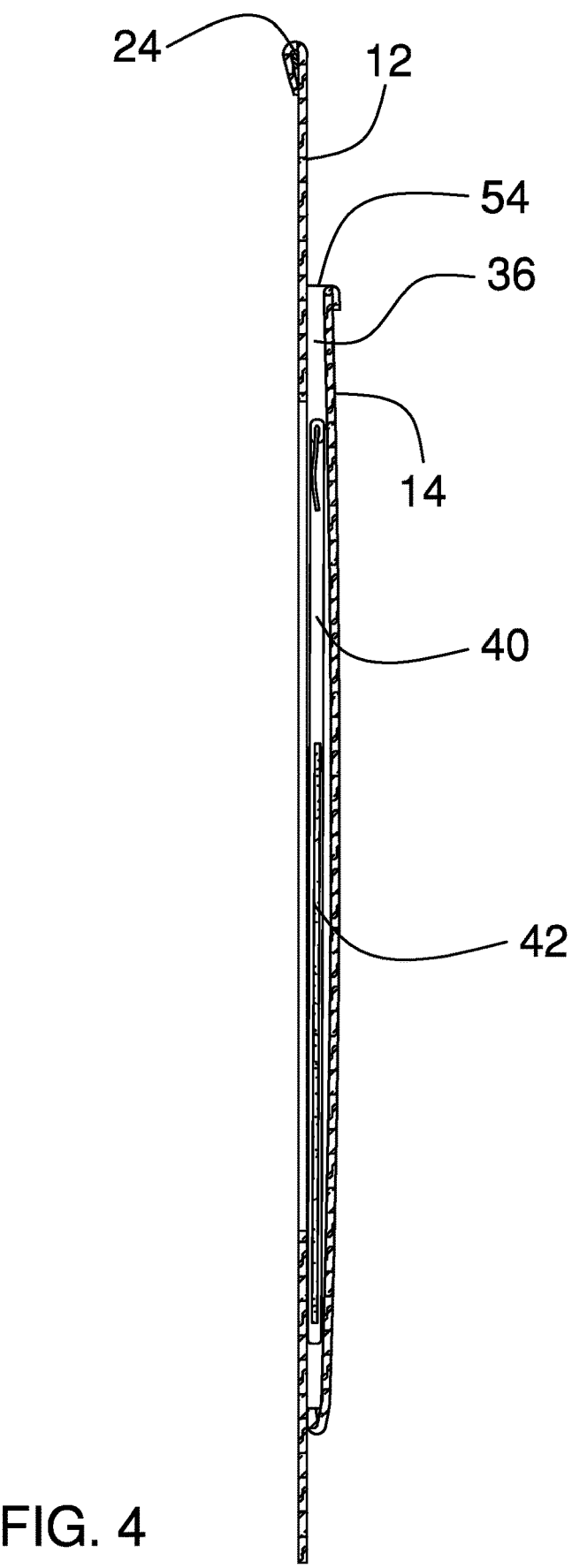
FIG. 4 is a cross-sectional view of an embodiment of the disclosure.
Figure 5:
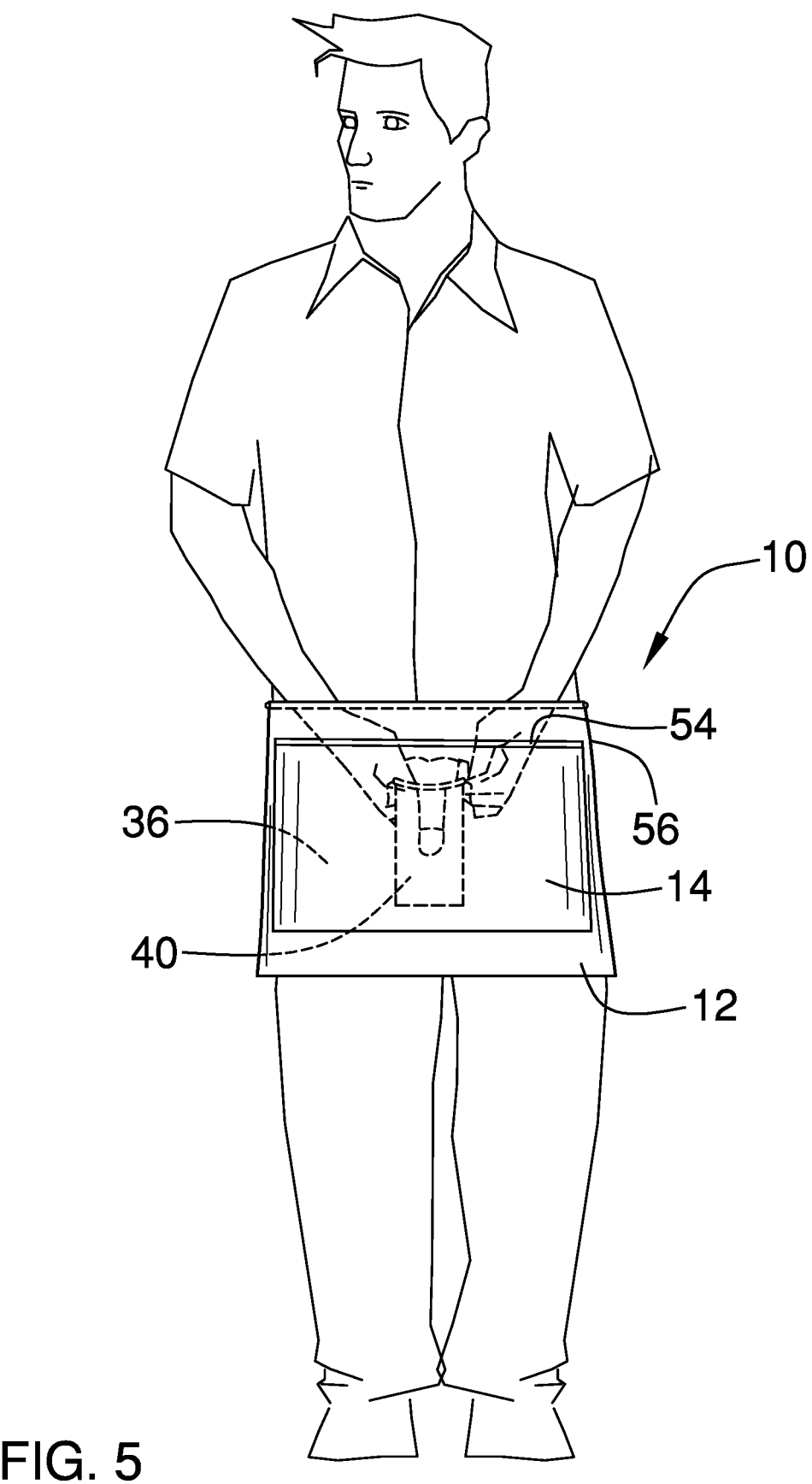
FIG. 5 is an in-use view of an embodiment of the disclosure.

With reference now to the drawings, and in particular to FIGS. 1 through 5 thereof, a new concealment device embodying the principles and concepts of an embodiment of the disclosure and generally designated by the reference numeral 10 will be described.

As best illustrated in FIGS. 1 through 5, the user wearable urinal bag concealment device 10 generally comprises a first panel 12 and a second panel 14. The first panel 12 and the second panel 14 are flexible so that the first panel 12 and the second panel 14 are selectively rollable and foldable. The first panel 12 and the second panel 14 are substantially rectangularly shaped. The first panel 12 has an upper limit 16, a lower limit 18, and opposing side limits 20.

A plurality of couplers 22 is coupled to the upper limit 16 of the first panel 12. The plurality of couplers 22 is configured to couple the first panel 12 to a male user so that the first panel 12 is positioned over and substantially conceals a groin area of the male user.

A sleeve 24 is coupled to the upper limit 16 of the first panel 12. The plurality of couplers 22 comprises a line 26 that is positioned through the sleeve 24 so that opposing terminal sections 28 of the line 26 extend from the opposing side limits 20 of the first panel 12. The opposing terminal sections 28 are configured to loopedly position around a waist of the male user, positioning the male user to tie the opposing terminal sections 28 to couple the line 26 to the user so that the first panel 12 substantially conceals the groin area of the male user.

The second panel 14 has a lower edge 30 and opposing side edges 32 that are coupled to a front face 34 of the first panel 12 to define a pouch 36 that is accessible at an upper edge 38 of the second panel 14. The pouch 36 is configured to position a urinal bag 40. While any commercially available urinal bag 40 may be used with the disclosed device 10, it is anticipated that a urinal bag 40 containing a pad 42 comprising a superabsorbent polymer 44 will be preferred.

A slot 46 is positioned in the first panel 12. The slot 46 is parallel to the opposing side limits 20 of the first panel 12. The pouch 36 is configured to insert hands of the male user, positioning the male user to manipulate a penis of the male user through the slot 46 into an open end 48 of the urinal bag 40 so that the urinal bag 40 is configured to collect urine that is excreted through the penis. The device 10 fulfills the needs of a user who require a means to discretely urinate in a public setting. The device 10, having the appearance of a standard apron 56, is optimally suited to fulfill this unmet need.

The lower edge 30 of the second panel 14 is separated from the lower limit 18 of the first panel 12 by from 2.5 centimeter to 7.5 centimeters. The lower edge 30 is separated from the lower limit 18 by 5.1 centimeters.

The first panel 12 and the second panel 14 may be of a variety of sizes so as to cover and substantially conceal the groin area, as well as the upper legs, of male users of a variety of sizes. In a first example, the upper limit 16 and the lower limit 18 of the first panel 12 may be separated by 38.0 centimeters to 58.0 centimeters while the opposing side limits 20 of the first panel 12 may be separated by 38.0 centimeters to 100.0 centimeters. In the first example, the upper edge 38 and the lower edge 30 of the second panel 14 may be separated by from 25.0 centimeters to 46.0 centimeters while the opposing side edges 32 of the second panel 14 may be separated by from 45.0 centimeters to 80.0 centimeters. Also, in the first example, the slot 46 may measure from 15.0 centimeters to 35.0 centimeters and the opposing terminal sections 28 may have a combined length of from 75.0 centimeters to 170.0 centimeters. The lower limits of the configuration of the first example would be suited for a small bodied male user, such as a young male, while the upper limits of this configuration would be suited for a large bodied male.

In a second example, the upper limit 16 and the lower limit 18 of the first panel 12 may be separated by from 43.0 centimeters to 53.0 centimeters, while the opposing side limits 20 of the first panel 12 may be separated by from 58.0 centimeters to 94.0 centimeters. In the second example, the upper edge 38 and the lower edge 30 of the second panel 14 may be separated by from 30.0 centimeters to 40.0 centimeters, while the opposing side edges 32 of the second panel 14 may be separated by from 55.0 centimeters to 70.0 centimeters. Also, in the second example, the slot 46 may measure from 20.0 centimeters to 30.0 centimeters and the opposing terminal sections 28 may have a combined length of from 125.0 centimeters to 160.0 centimeters.

In a third example, the upper limit 16 and the lower limit 18 of the first panel 12 are separated by 48.3 centimeters, while the opposing side limits 20 of the first panel 12 are separated by 76.2 centimeters. In the third example, the upper edge 38 and the lower edge 30 of the second panel 14 are separated by 35.6 centimeters, while the opposing side edges 32 of the second panel 14 are separated by 61.0 centimeters. Also, in the third example, the slot 46 measures 25.4 centimeters and the opposing terminal sections 28 have a combined length of 152.4 centimeters.

A first seam 50 is coupled to and extends between the first panel 12 and the second panel 14. The first seam 50 extends perpendicularly from the upper edge 38 of the second panel 14 toward the lower edge 30 so that the pouch 36 mimics a pair of pockets 52, with each pocket 52 having an associated opening 54. The first seam 50 measures from one centimeter to five centimeters. The first seam 50 not only renders the pouch 36 into the pair of pockets 52 so that the device 10 is in the form of an apron 56, it also serves to keep the upper edge 38 of the second panel 14 in proximity to the first panel 12, reducing the likelihood of a person proximate to the male user observing the hands of the user within the pouch 36.

A second seam 58 is coupled to and extends between the first panel 12 and the second panel 14. The second seam 58 is aligned with the first seam 50 and extends from the lower edge 30 of the second panel 14 toward the first seam 50 so that the pouch 36 further mimics the pair of pockets 52. The second seam 58 measures from one centimeter to five centimeters.

In use, the male user couples the device 10 around his waist of by looping the line 26 around his waist and tying it at his back. The urinal bag 40 is positioned in the pouch 36 proximate to the slot 46. When the male user needs to urinate, he insert his hands into the pouch 36 through the pair of openings 54 and manipulates his penis of through the slot 46 into the open end 48 of the urinal bag 40, wherein the urine is collected.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A user wearable urinal bag concealment device comprising:
   a first panel;
   a plurality of couplers coupled to an upper limit of the first panel wherein the plurality of couplers is configured for coupling the first panel to a male user such that the first panel is positioned over and conceals a groin area of the male user;
   a second panel having a lower edge and opposing side edges coupled to a front face of the first panel defining a pouch accessible at an upper edge of the second panel wherein the pouch is configured for positioning a urinal bag;
   a slot positioned in the first panel wherein the pouch is configured for inserting hands of the male user positioning the male user for manipulating a penis of the male user through the slot into an open end of the urinal bag such that the urinal bag is configured for collecting urine excreted through the penis; and
   a first seam coupled to and extending between the first panel and the second panel, the first seam extending perpendicularly from the upper edge of the second panel toward a lower edge of the second panel, the first seam having a length less than a length from said upper edge of said second panel to said lower edge of said second panel such that the pouch mimics a pair of pockets with each pocket having an associated opening; and a second seam coupled to and extending between the first panel and the second panel, the second seam being aligned with the first seam and extending from the lower edge of the second panel toward the first seam such that the pouch mimics the pair of pockets.

2. The device of claim 1, further including the first panel and the second panel being flexible such that the first panel and the second panel are selectively rollable and foldable.

3. The device of claim 1, further including the first panel and the second panel being rectangularly shaped.

4. The device of claim 3, further comprising:
the first panel having a lower limit and opposing side limits, the upper limit and the lower limit being separated by from 38.0 centimeters to 58.0 centimeters, the opposing side limits being separated by from 38.0 centimeters to 100.0 centimeters;
the upper edge and the lower edge being separated by from 25.0 centimeters to 46.0 centimeters, the opposing side edges being separated by from 45.0 centimeters to 80.0 centimeters; and
the slot measuring from 15.0 centimeters to 35.0 centimeters.

5. The device of claim 4, further comprising:
the upper limit and the lower limit being separated by from 43.0 centimeters to 53.0 centimeters, the opposing side limits being separated by from 58.0 centimeters to 94.0 centimeters;
the upper edge and the lower edge being separated by from 30.0 centimeters to 40.0 centimeters, the opposing side edges being separated by from 55.0 centimeters to 70.0 centimeters; and
the slot measuring from 20.0 centimeters to 30.0 centimeters.

6. The device of claim 4, further comprising:
the upper limit and the lower limit being separated by 48.3 centimeters, the opposing side limits being separated by 76.2 centimeters;
the upper edge and the lower edge being separated by 35.6 centimeters, the opposing side edges being separated by 61.0 centimeters; and
the slot measuring 25.4 centimeters.

7. The device of claim 4, further including the lower edge being separated from the lower limit by from 2.5 centimeter to 7.5 centimeters.

8. The device of claim 7, further including the lower edge being separated from the lower limit by 5.1 centimeters.

9. The device of claim 1, further including a sleeve coupled to the upper limit of the first panel, the plurality of couplers comprising a line positioned through the sleeve such that opposing terminal sections of the line extend from opposing side limits of the first panel wherein the opposing terminal sections are configured for loopedly positioning around a waist of the male user positioning the male user for tying the opposing terminal sections for coupling the line to the user such that the first panel conceals the groin area of the male user.

10. The device of claim 9, further including the opposing terminal sections having a combined length of from 75.0 centimeters to 170.0 centimeters.

11. The device of claim 10, further including the opposing terminal sections having a combined length of from 125.0 centimeters to 160.0 centimeters.

12. The device of claim 11, further including the opposing terminal sections having a combined length of 152.4 centimeters.

13. The device of claim 1, further including the first seam measuring from one centimeter to five centimeters.

14. The device of claim 1, further including the second seam measuring from one centimeter to five centimeters.

15. The device of claim 1, further including the slot being parallel to opposing side limits of the first panel.

16. A user wearable urinal bag concealment device and urinal bag combination comprising:
a first panel;
a plurality of couplers coupled to an upper limit of the first panel wherein the plurality of couplers is configured for coupling the first panel to a male user such that the first panel is positioned over and conceals a groin area of the male user;
a second panel having a lower edge and opposing side edges coupled to a front face of the first panel defining a pouch accessible at an upper edge of the second panel;
a urinal bag positioned in the pouch;
a slot positioned in the first panel wherein the pouch is configured for inserting hands of the male user positioning the male user for manipulating a penis of the male user through the slot into an open end of the urinal bag such that the urinal bag is configured for collecting urine excreted through the penis; and
a first seam coupled to and extending between the first panel and the second panel, the first seam extending perpendicularly from the upper edge of the second panel toward a lower edge of the second panel, the first seam having a length less than a length from said upper edge of said second panel to said lower edge of said second panel such that the pouch mimics a pair of pockets with each pocket having an associated opening; and a second seam coupled to and extending between the first panel and the second panel, the second seam being aligned with the first seam and extending from the lower edge of the second panel toward the first seam such that the pouch mimics the pair of pockets.

17. A user wearable urinal bag concealment device comprising:
a first panel, the first panel being flexible such that the first panel is selectively rollable and foldable, the first panel being rectangularly shaped, the first panel having an upper limit, a lower limit, and opposing side limits, the upper limit and the lower limit being separated by from 38.0 centimeters to 58.0 centimeters, the opposing side limits being separated by from 38.0 centimeters to 100.0 centimeters, the upper limit and the lower limit being separated by from 43.0 centimeters to 53.0 centimeters, the opposing side limits being separated by from 58.0 centimeters to 94.0 centimeters, the upper limit and the lower limit being separated by 48.3 centimeters, the opposing side limits being separated by 76.2 centimeters;
a plurality of couplers coupled to the upper limit of the first panel wherein the plurality of couplers is configured for coupling the first panel to a male user such that the first panel is positioned over and conceals a groin area of the male user;
a sleeve coupled to the upper limit of the first panel, the plurality of couplers comprising a line positioned through the sleeve such that opposing terminal sections of the line extend from the opposing side limits of the first panel wherein the opposing terminal sections are configured for loopedly positioning around a waist of the male user positioning the male user for tying the opposing terminal sections for coupling the line to the user such that the first panel conceals the groin area of the male user, the opposing terminal sections having a combined length of from 75.0 centimeters to 170.0 centimeters, the opposing terminal sections having a combined length of from 125.0 centimeters to 160.0 centimeters, the opposing terminal sections having a combined length of 152.4 centimeters;

a second panel having a lower edge and opposing side edges coupled to a front face of the first panel defining a pouch accessible at an upper edge of the second panel wherein the pouch is configured for positioning a urinal bag, the second panel being flexible such that the second panel is selectively rollable and foldable, the second panel being rectangularly shaped, the lower edge being separated from the lower limit by from 2.5 centimeters to 7.5 centimeters, the lower edge being separated from the lower limit by 5.1 centimeters, the upper edge and the lower edge being separated by from 25.0 centimeters to 46.0 centimeters, the opposing side edges being separated by from 45.0 centimeters to 80.0 centimeters, the upper edge and the lower edge being separated by from 30.0 centimeters to 40.0 centimeters, the opposing side edges being separated by from 55.0 centimeters to 70.0 centimeters, the upper edge and the lower edge being separated by 35.6 centimeters, the opposing side edges being separated by 61.0 centimeters;

a first seam coupled to and extending between the first panel and the second panel, the first seam extending perpendicularly from the upper edge of the second panel toward the lower edge, the first seam having a length less than a length from said upper edge of said second panel to said lower edge of said second panel such that the pouch mimics a pair of pockets with each pocket having an associated opening, the first seam measuring from one centimeter to five centimeters;

a second seam coupled to and extending between the first panel and the second panel, the second seam being aligned with the first seam and extending from the lower edge of the second panel toward the first seam such that the pouch mimics the pair of pockets, the second seam measuring from one centimeter to five centimeters; and a slot positioned in the first panel wherein the pouch is configured for inserting hands of the male user positioning the male user for manipulating a penis of the male user through the slot into an open end of the urinal bag such that the urinal bag is configured for collecting urine excreted through the penis, the slot being parallel to the opposing side limits of the first panel, the slot measuring from 15.0 centimeters to 35.0 centimeters, the slot measuring from 20.0 centimeters to 30.0 centimeters, the slot measuring 25.4 centimeters.

* * * * *